United States Patent [19]

Donzis

[11] Patent Number: 5,519,009
[45] Date of Patent: May 21, 1996

[54] SOLUBILIZED YEAST GLUCAN

[76] Inventor: Byron A. Donzis, 3008 Rogerdale, Houston, Tex. 77042

[21] Appl. No.: 131,457

[22] Filed: Oct. 1, 1993

[51] Int. Cl.⁶ .............................................. A61K 31/7155
[52] U.S. Cl. ................ 514/054; 536/123.1; 536/123.12
[58] Field of Search .......................... 536/123.12, 123.1; 514/54

[56] References Cited

U.S. PATENT DOCUMENTS

| | | | |
|---|---|---|---|
| 3,759,896 | 9/1973 | Komatsu | 536/124 |
| 3,856,775 | 12/1974 | Fukuoka | 536/123.12 |
| 3,883,505 | 5/1975 | Hamuro | 536/124 |
| 4,207,312 | 6/1980 | Fujii | 514/23 |
| 4,454,315 | 6/1984 | Sasaki | 536/123.12 |
| 4,707,471 | 11/1987 | Larm et al. | 514/54 |
| 4,766,207 | 8/1988 | Deger et al. | 536/124 |
| 4,810,646 | 3/1989 | Jamas et al. | 536/123.12 |
| 4,833,131 | 5/1989 | Williams et al. | 514/54 |
| 4,950,749 | 8/1990 | Johal et al. | 536/127 |
| 4,960,697 | 10/1990 | Johal | 435/101 |
| 4,973,581 | 11/1990 | Matsuzaki | 514/54 |
| 5,106,967 | 4/1992 | Mazur | 536/119 |
| 5,223,491 | 6/1993 | Donzis | 514/54 |

FOREIGN PATENT DOCUMENTS

| | | |
|---|---|---|
| 60-255733 | 12/1985 | Japan . |
| 2076418 | 12/1981 | United Kingdom . |
| 91/03495 | 3/1991 | WIPO . |

OTHER PUBLICATIONS

Browder, *Ann. Surg.*, May 1990, pp. 605–613.
Davidson, *JAMA*, 265:1833–1839, 1991.
Gallin, *Int. J. Immunopharmac.*, 14:173–183, 1992.
Rasmussen, *Scand. J. Immunol.*, 32:333–340, 1990.
Rasmussen, *J. of Cellular Biochemistry*, 46:60–68, 1991.
Sakurai, *Int. J. Immunopharmac.*, 14:821–830, 1992.
Suzuki, *Int. J. Immunopharmac.*, 12:675–684, 1990.
Tanaka, *Immunopharmac. and Immunotoxi.*, 14:403–420, 1992.

*Primary Examiner*—Michael G. Wityshyn
*Assistant Examiner*—Everett White
*Attorney, Agent, or Firm*—Sue Z. Shaper; Butler & Binion

[57] ABSTRACT

Sorbitol-solubilized yeast glucan, its method of preparation, and methods of use.

18 Claims, No Drawings

SOLUBILIZED YEAST GLUCAN

FIELD OF THE INVENTION

This invention relates to a method for producing solubilized yeast glucan, to compositions comprising sorbitol-solubilized yeast glucan, and to methods of using sorbitol-solubilized yeast glucan.

BACKGROUND OF THE INVENTION:

Glucans are polymers of glucose which may be derived from the cell walls of yeast. Yeast glucans containing a beta (1,3)-linked glucopyranose backbone have been known to have biological activity, specifically they have been shown to activate the immune system across kingdom lines.

Neutral beta (1,3) glucan polymers are limited in their utility, for example in foodstuffs and pharmaceutical compositions, because they are not readily soluble in aqueous, physiological media. Attempts to develop soluble beta (1,3) glucans thus far depend upon chemical substitution with charged groups, such as phosphate (see U.S. Pat. No. 4,707,471) or other functional groups such as sulphate, which change the native conformation of the glucan molecules and may alter their biological and pharmacokinetic properties.

SUMMARY OF THE INVENTION

The present invention is a method of producing solubilized glucan. An aqueous solution of sorbitol is heat treated and clarified. Insoluble glucan is added to the treated sorbitol solution and the mixture heated to produce a solubilized glucan product.

Sorbitol solubilized glucan is used to produce soluble glucan compositions for a wide variety of applications. Sorbitol solubilized glucan is useful in pharmaceutical, nutritional, and cosmetic applications. It may be administered orally, intravenously, intramuscularly, nasally, subcutaneously, topically, and by other means known for effective administration of a solubilized product.

Glucan produced by the sorbitol-solubilization method is a safe, potent immune system enhancer when administered to an animal. Safe and efficacious preparations of soluble glucan polymers of the present invention may be used in therapeutic and/or nutritional treatment of individuals to stimulate their immune system.

Sorbitol solubilized glucan may be added to foodstuffs and beverages for its beneficial effects on health as a general immune stimulator. Sorbitol solubilized glucan is used to formulate pharmaceutical compositions without the problems inherent in the insoluble glucan. Using the sorbitol soluble glucan of the present invention, it is now possible to produce a great variety of products for ingestion or other route of administration to animals such as humans, domestic farm animals, domestic pets and including birds, fish, and crustaceans, containing the healthful glucan additive.

DESCRIPTION OF THE INVENTION

The soluble glucan preparations of the present invention are prepared from insoluble glucan particles. Preferably, insoluble glucans derived from yeast cell walls are used. Glucan particles which are particularly useful in the present invention are predominantly beta (1,3) glucans prepared as described in U.S. Pat. No. 5,223,491 to Donzis, and commercially available under the trade name NAYAD from Immudyne Inc., Houston, Tx.

In the method of the present invention, an aqueous solution of sorbitol is heated resulting in a cloudy solution. The solution is left to cool, e.g., overnight, to form a clear and colorless solution. The sorbitol solution is then reheated and insoluble glucan is added. The solution will appear soluble, e.g., clear, after continued heating and stirring. The clear solution is then permitted to cool. The final product may turn from colorless and clear to gray-white and cloudy in appearance.

The aqueous sorbitol solution may contain approximately 5–91% sorbitol, e.g., useful solutions may be approximately 20–80% sorbitol, preferably approximately 40–80% or 50–75%, and most preferably approximately 70%. Increasing the percentage of sorbitol results in the ability to solubilize a greater mass of glucan per volume of sorbitol solution and/or less time required to solubilize a given mass of glucan. Depending upon the requirements of the solubilized glucan product, e.g., mass of glucan needed to be solubilized per unit volume or upon the requirements of the preparation process, e.g., speed of solubilization, the percentage of sorbitol in the solubilizing solution will vary.

The amount of insoluble glucan per 100 ml of sorbitol solution will be less than approximately 100 mg, and preferably approximately equal to or less than 50 mg, and most preferably approximately equal to or less than 10 mg. The mass of glucan able to be solubilized in the sorbitol solution will vary with the percentage of sorbitol used, and the time for heating and stirring the glucan-sorbitol mixture.

The temperature and time required to solubilize the glucan product may vary. The sorbitol is generally heated to a temperature in the range of approximately 35°–70° C., preferably approximately 40°–60° C., and most preferably at approximately 50° C. The time required to preheat the sorbitol is that required to produce a cloudy solution, e.g., approximately 2 hours at 50° C. This time will increase when the solution is heated at a lower temperature, and decrease when the solution is heated at a higher temperature.

The time required for the preheated sorbitol solution to cool and clear may vary. When cooling at room temperature, the solution will become colorless or clear within approximately 8 hours.

The insoluble glucan is heated in the sorbitol solution for a time and at a temperature sufficient to solubilize the glucan, as evidenced by the formation of a colorless, clear solution. The solubilizing temperature will be in the range of approximately 35°–70° C., preferably approximately 40°–60° C. and most preferably at approximately 50° C. The time required to solubilize the glucan is that required to produce a clear and colorless solution, e.g., approximately 30 minutes at 50° C. This time will increase when the solution is heated at a lower temperature, and decrease when the solution is heated at a higher temperature.

The sorbitol-solubilized glucan product is in the form of a neutral aqueous solution of immunologically active glucans which is suitable for oral, nasal, parenteral or other known route of administration of a soluble composition to animals. The sorbitol-solubilized glucan product provides soluble glucan for addition to foodstuffs, cosmetics, and pharmaceutical compositions.

The sorbitol-solubilized glucan composition of the present invention may be administered to animals including domestic pets and livestock, fish, birds and crustaceans, as well as humans. Various foodstuffs including prepared foods, beverages, nutritional supplements may be prepared containing sorbitol-solubilized glucan. Pharmaceutical compositions may be prepared containing sorbitol-solubilized glucan.

The sorbitol-solubilized glucans of the present invention are immunologically active. Such compositions may be screened for beneficial immunological activity, for example, by administration of the sorbitol-solubilized glucan to a model animal, e.g., mouse, and analyzing the reaction of the model animal's immune system to the administered glucan product, e.g, by measuring the level of IL-1 or similar immunoregulatory agent in the injected animal's blood post-injection.

The invention is further illustrated by reference to the following examples:

Example 1

Preparation of Sorbitol-Solubilized Glucan

Sorbitol is commercially available in dry form or as a 91% or 70% solution. The required percent solution may be prepared by dissolving a specified mass of dry sorbitol in the appropriate volume of water, or by diluting the 91 or 70% solutions with the appropriate volume of water.

Seventy percent aqueous sorbitol was prepared in water by appropriate dilution of 91% sorbitol. A volume of 100 ml of the 70% sorbitol solution was heated to 50° C. for approximately 2 hours. The resulting cloudy solution was left to stand overnight at room temperature, after which time a clear and colorless solution remained, having an approximate volume of 75 ml. The sorbitol solution was reheated to approximately 50° C. and 3.75 g (5%) insoluble glucan (NAYAD, ImmuDyne, Houston, Tx.) was added. The glucan-sorbitol mixture was heated with stirring for approximately 30 minutes, at which time the solution appeared colorless and clear. The sorbitol solubilized-glucan was permitted to cool, resulting in a gray-white, cloudy solution containing approximately 50 mg glucan/ml.

Example 2

Immunostimulation by Sorbitol-Solubilized Glucan

To evaluate the immunostimulating activity of sorbitol-solubilized glucan (SSG), the ability of this composition to induce IL-1 in model animals was analyzed. Glucan was solubilized as described for example 1, using 1 g of glucan per 100 ml of 70% sorbitol, and resulting in a solubilized glucan containing approximately 10 mg glucan/ml.

ICR Outbred mice, each weighing approximately 25 g and obtained from SASCO, Houston Tx., were divided among test groups having 5 mouse per group as follows:

Group 1 - 20 ug Lipopolysaccharide in 100 ul $dH_2O$;
Group 2 - 100 ul $dH_2O$ orally and 100 ul $dH_2O$ i.p.;
Group 3 - 100 ul SSG (10 mg/ml) i.p.;
Group 4 - 100 ul SSG (10 mg/ml) orally
i.p. - intraperitoneal injection Two mice in each test group were sacrificed at 24 hours post SSG treatment, and the remaining three were sacrificed at 72 hours post SSG treatment. Each animal's blood was collected, permitted to clot, and the serum tested by ELISA for the presence of IL-1.

The ELISA, enzyme-linked immunosorbant assay was prepared as a kit commercially available from Genzyme Corp. (Cambridge, Mass), having the trade name Intertest-1 alpha Elisa Kit, and utilized a conventional double antibody technique. The first antibody was an anti-mouse IL-1 alpha antibody with a biotinylated second antibody. Correlation coefficients for assay standard curves were 0.96 and 0.98, respectively for serum and non-serum containing samples. The results of the ELISA are shown in Table 1.

TABLE 1

| Test Group | IL-1 (pg/ml) | |
|---|---|---|
| | 24 hours | 72 hours |
| 1 | | |
| Positive Control | 40 | 0 |
| LPS, i.p. | 101 | 0 |
| 2 | | |
| Negative Control | 0 | 0 |
| $H_2O$, i.p. and orally | 0 | 0 |
| 3 | 0 | 0 |
| SSG, 10 mg/ml i.p. | 0 | 0 |
| 4 | 94 | 0 |
| SSG, 10 mg/ml orally | 25 | 0 |

The stimulatory effect of soluble glucan is transitory, evident at 24 hours but absent at 72 hours post treatment. Failure in this experiment to detect IL-1 in the serum of animals treated with SSG by i.p. injection is postulated to have occurred due to faster action of the stimulator and faster clearance of IL-1. It is expected that examination of earlier time periods will demonstrate effective action of SSG in stimulating IL-1 when administered by i.p. injection.

EXAMPLE 3

Method for Screening SSG Solutions

A range of SSG solutions is prepared by varying the percentage of sorbitol, (e.g. from 5 to 80%) and by varying the mass of glucan solubilized (e.g. up to 100 mg per ml).

The SSG preparations are administered orally or by injection to host animals, and the animals response to the administration is monitored and analyzed thereafter. Preferably, analysis includes evaluation of the treated animal's blood or serum for the presence of immunomodulatory agents including IL-1, by Eliza or other methods common in the field. The presence of IL-1 in the test animal's blood or serum is correlated with an immunologically active composition.

Example 4

Preparation of Foodstuffs Containing SSG

The SSG solution prepared as in Examples 1 or 3 may be diluted in aqueous medium or added neat in the preparation of foodstuffs or beverages. For example, a volume of SSG is added to milk, juice, mineral water, infant formula, liquid nutritional supplements, carbonated beverages, and the like, to breads, peanut butter, cheese, jams, soups, and the like, and to vitamins, anti-oxidants and the like. In a preferred embodiment, SSG is added to animal feed, for example feed for domestic farm animals, pets, including birds, fish and crustaceans.

I claim:

1. A method for stimulating the production of interleukin-1 (IL-1) in an animal comprising:
   administering to an animal an effective IL-1 stimulating dose of a yeast glucan containing predominantly beta (1,3) glycosidic linkages solubilized in an aqueous sorbitol solution.

2. The method of claim 1, wherein said sorbitol is in solution in an amount ranging from 5% to 91% by volume.

3. The method of claim 1, wherein said sorbitol is in an amount ranging from 20% to 85% by volume.

4. The method of claim 1, wherein said sorbitol is in solution in an amount ranging from 40% to 80% by volume.

5. The method of claim 1, wherein said sorbitol is in solution in an amount of 70% by volume.

6. The method of claim 1, wherein said glucan is in an amount less than 100 mg/ml.

7. The method of claim 1, wherein said glucan is in an amount less than 50 mg/ml.

8. The method of claim 1, wherein said glucan is in an amount less than 10 mg/ml.

9. The method of claim 1, wherein said administration is orally, topically, nasally, rectally, intravenously, intramuscularly or intraperitoneally.

10. The method of claim 9, wherein said administration is orally.

11. The method of claim 1, wherein said animal is a human.

12. The method of claim 1, wherein said animal is a domestic farm animal.

13. The method of claim 1, wherein said animal is a domestic bird.

14. The method of claim 13, wherein said bird is a chicken or turkey.

15. The method of claim 1, wherein said animal is a domestic pet.

16. The method of claim 1, wherein said animal is a fish.

17. The method of claim 1, wherein said animal is a crustacean.

18. The method of claim 1, wherein said glucan is derived from yeast cell walls.

* * * * *